United States Patent [19]
Shimizu et al.

[11] Patent Number: 4,778,890
[45] Date of Patent: Oct. 18, 1988

[54] PROCESS FOR PREPARING NITRILES

[75] Inventors: Shinkichi Shimizu, Hirakata; Takayuki Shoji, Osaka; Nobuyuki Abe, Ikoma; Masanori Doba, Osaka; Akira Taguro, Yahata; Akira Iguchi; Toru Nakaishi, both of Osaka, all of Japan

[73] Assignee: Koei Chemical Co., Ltd., Osaka, Japan

[21] Appl. No.: 75,037

[22] Filed: Jul. 16, 1987

[30] Foreign Application Priority Data

Aug. 4, 1986 [JP] Japan ................ 61-183255
Sep. 16, 1986 [JP] Japan ................ 61-218485

[51] Int. Cl.$^4$ ............... C07D 241/24; C07D 213/57
[52] U.S. Cl. ................... 544/336; 546/286; 546/287
[58] Field of Search ........... 546/286, 287; 544/336; 558/322

[56] References Cited

U.S. PATENT DOCUMENTS

| | | | |
|---|---|---|---|
| 2,861,999 | 11/1958 | D'Alessandro | 546/286 |
| 3,297,587 | 1/1967 | Scherhag et al. | 546/286 X |
| 3,686,194 | 8/1972 | Hagedorn et al. | 546/286 |
| 3,812,171 | 5/1974 | Neikam et al. | 546/286 X |
| 3,845,094 | 10/1974 | Angstadt | 546/286 X |
| 4,124,631 | 11/1978 | Hayami et al. | 558/327 |
| 4,178,304 | 12/1979 | Litvishkov et al. | 558/327 |
| 4,336,205 | 6/1982 | Onishi et al. | 546/286 X |
| 4,530,797 | 7/1985 | Hayami et al. | 558/327 |
| 4,603,207 | 7/1986 | DiCosimo et al. | 546/286 |

FOREIGN PATENT DOCUMENTS

| | | | |
|---|---|---|---|
| 2810856 | 10/1979 | Fed. Rep. of Germany | 558/327 |
| 0013770 | 8/1967 | Japan | 558/327 |
| 820125 | 9/1959 | United Kingdom | 558/327 |
| 1060043 | 2/1967 | United Kingdom | 546/286 |
| 0787406 | 12/1980 | U.S.S.R. | 558/327 |

OTHER PUBLICATIONS

Forni, Applied Catalysis, 20 (1986), pp. 219-230.

Primary Examiner—Joseph Paul Brust
Attorney, Agent, or Firm—Wenderoth, Lind & Ponack

[57] ABSTRACT

A heteroaromatic nitrile is prepared in a high selectivity and yield by catalytically reacting an alkyl-substituted heteroaromatic compound with molecular oxygen and ammonia in a molar ratio of oxygen to ammonia of not larger than 1.6:1 in a gaseous phase in the presence of a catalyst comprising a vanadium-phosphorus oxide of the formula:

$$VP_xSb_yO_z \qquad (I)$$

wherein x, y and z represent atomic ratios of phosphorus, antimony and oxygen to vanadium, respectively, and x is from 0.1 to 5, y is 0 to 8 and z is defined from the valencies of other elements.

7 Claims, No Drawings

PROCESS FOR PREPARING NITRILES

The present invention relates to a process for preparing nitriles. More particularly, it relates to a process for producing a heteroaromatic nitrile comprising catalytically reacting an alkyl-substituted heteroaromatic compound with ammonia and molecular oxygen in a gaseous phase (namely, by ammoxidation).

The heteroaromatic nitriles are useful as starting materials for the preparation of medicines or agricultural chemicals.

For catalyzing ammoxidation of an alkyl-substituted aromatic compound to prepare an aromatic nitrile, a number of catalysts comprising vanadium oxide are proposed. However, the conventional catalysts have too strong catalytic activity for the ammoxidation of alkyl-substituted heteroaromatic compounds, abnormal reactions such as dealkylation or cleavage of the heteroaromatic ring and therefore the objective nitriles are prepared in a low selectivity and yield.

Japanese Patent Publication No. 19706/1982 discloses, as a catalyst for ammoxidation of the alkyl-substituted heteroaromatic compound, a catalyst comprising antimony oxide, vanadium oxide and an oxide of a metal selected from the group consisting of iron, copper, titanium, cobalt, manganese and nickel. Although this catalyst has a comparatively high selectivity, it suffers from a decrease of catalytic activity through reduction with ammonia and is not satisfactory for industrial production.

As a result of the extensive study, it has been found that, in the preparation of the heteroaromatic nitriles by ammoxidation of the alkyl-substituted heteroaromatic compounds, the abnormal reactions can be suppressed and the heteroaromatic nitriles can be prepared in a high selectivity and yield when a molar ratio of molecular oxygen and ammonia is selected and a vanadium-phosphorus base compound is used as a catalyst, and further said catalyst has good resistance against heat and reduction and is safe in operation. The present invention is completed based on these findings.

According to the present invention, there is provided a process for preparing a heteroaromatic nitrile comprising catalytically reacting an alkyl-substituted heteroaromatic compound with molecular oxygen and ammonia in a molar ratio of oxygen to ammonia of not larger than 1.6:1 in a gaseous phase in the presence of a catalyst comprising an oxide of the formula:

$$VP_xSb_yO_z \qquad (I)$$

wherein x, y and z represent atomic ratios of phosphorus, antimony and oxygen to vanadium, respectively, and x is from 0.1 to 5, y is 0 to 8 and z is defined from the valencies of other elements.

The catalyst to be used according to the present invention may be any one containing the oxide (I). A vanadium-phosphorus oxide, namely the oxide (I) wherein y is 0 (zero) can be used in the amorphous or crystalline form according to the present invention. When the vanadium-phosphorus oxide is amorphous, an atomic ratio of vanadium and phosphorus is not critical. Preferably, said ratio is from 1:0.5 to 1:3. As the crystalline vanadium-phosphorus oxide, one in which the atomic ratio of vanadium and phosphorus is 1, 2, 3 and the like is known. Among them, one in which the atomic ratio of vanadium and phosphorus is 1 and/or a reduction product of such vanadium-phosphorus oxide are effective in the process according to the present invention.

The crystalline oxide used herein is represented by the formula:

$$(VO)_nP_nO_{4n-1} \cdot xH_2O \qquad (II)$$

wherein n is an integer not less than 2 and x is 0 or a positive integer. In the formula (II), the valency of vanadium is 4 or 5.

Specific examples of the compound (II) are alpha-vanadyl phosphate (alpha-VOPO$_4$), alpha-vanadyl phosphate dihydrate (alpha-VOPO$_4$·2H$_2$O), beta-vanadyl phosphate (beta-VOPO$_4$), vanadyl pyrophosphate ((VO)$_2$P$_2$O$_7$) and vanadyl pyrophosphate hydrate ((VO)$_2$H$_4$P$_2$O$_9$ or (VO)$_2$P$_2$O$_7$·2H$_2$O), X-ray diffraction patterns of which are shown in Table 1.

TABLE 1

| Alpha-VOPO$_4$ d (Å) | Alpha-VOPO$_4$·2H$_2$O d (Å) | Beta-VOPO$_4$ d (Å) | (VO)$_2$P$_2$O$_7$ d (Å) | (VO)$_2$H$_4$P$_2$O$_9$ d (Å) |
|---|---|---|---|---|
| 4.37 | 7.41 | 5.18 | 6.28 | 5.625 |
| 4.11 | 4.76 | 4.60 | 5.65 | 4.761 |
| 3.100 | 4.37 | 3.96 | 4.79 | 4.058 |
| 3.000 | 3.70 | 3.89 | 3.87 | 3.659 |
| 2.193 | 3.18 | 3.48 | 2.982 | 3.275 |
| 1.963 | 3.105 | 3.40 | 2.906 | 3.093 |
| 1.550 | 2.863 | 3.18 | 2.655 | 2.92 |
| 1.517 | 2.833 | 3.068 | 2.435 | 2.777 |
| 1.461 | 2.379 | 2.974 | 2.399 | |
| | 2.197 | 2.640 | 2.362 | |
| | 2.108 | 2.410 | 2.271 | |
| | | 2.209 | 2.204 | |
| | | 2.172 | 2.083 | |
| | | 2.093 | | |

A vanadium-phosphorus oxide prepared by the reduction of these compounds has generally less crystallinity. This may be due to formation of lattice defects or shear structures.

The vanadium-phosphorus oxide (the oxide (I) wherein y is 0) may be prepared by a per se know method for preparing an oxide of vanadium and phosphorus. For example, the amorphous vanadium-phosphorus oxide is prepared by reacting ammonium metavanadate dissolved in an aqueous solution of ethanolamine with phosphoric acid and evaporating a reaction mixture to dryness and calcining the dried product in the air. The crystalline vanadium-phosphorus oxide is prepared by reacting vanadium pentoxide with phosphoric acid, evaporating a reaction mixture to dryness and calcining the dried product in the air, by reacting ammonium metavanadate with phosphoric acid, evaporating a reaction mixture to dryness and calcining the dried product in the air, or by reacting vanadium pentoxide, oxalic acid and ammonium dihydrogenphosphate, evaporating a reaction mixture to dryness and calcining the dried product in nitrogen.

A vanadium-phosphorus oxide prepared by reducing the crystalline oxide with a reducing gas such as hydrogen, ammonia or hydrocarbons may be used as a catalyst according to the present invention. For example, the crystalline oxide is preferably reduced by treating it with ammonia or an ammonia-containing gas at a temperature of 300° to 600° C.

Among the oxide (I) wherein y is not 0 (zero), those wherein x is from 0.2 to 1.5 and y is from 2 to 4 are preferred. The oxide (I) wherein y is not 0 may also be prepared by a per se known method for preparing an oxide of vanadium and phosphorus. For example, the oxide is prepared by adding a vanadium compound, a phosphorus compound and an antimony compound and optionally a carrier to water, evaporating the mixture to dryness and calcining it at a temperature of 450° to 800° C. in the air or an inactive gas for several to 20 hours.

For the preparation of the catalyst, any compound of each element can be used. Specific examples of the vanadium compound are ammonium metavanadate, vanadium pentoxide, vanadium phosphate, etc. Specific examples of the phosphorus compound are phosphoric acid, metaphosphoric acid, phosphorous acid, phosphate (such as ammonium phosphates), etc. Specific examples of the antimony compound are metal antimony, diantimony trioxide, diantimony pentoxide, antimony trichloride, etc.

The catalyst used according to the present invention may be carried on a carrier such as silica, alumina, silicon carbide, titanium oxide, diatomaceous earth and zeolite.

The alkyl-substituted heteroaromatic compound used according to the present invention includes a compound of the formula:

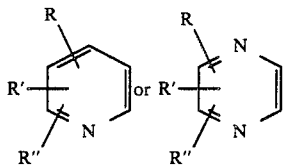

wherein R, R' and R'' are the same or different and each a hydrogen atom or a lower alkyl group having 1 to 4 carbon atoms with the proviso that at least one of them is the alkyl group. Specific examples of the alkyl-substituted heteroaromatic compound are 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2-methyl-5-ethylpyridine, 2,4,6-trimethylpyridine, 2,3,4-trimethylpyridine, 2,3,5-trimethylpyridine, 2,3,6-trimethylpyridine, methylpyrazine, ethylpyrazine, 2,3-dimethylpyrazine, 2,5-dimethylpyrazine, 2,6-dimethylpyrazine, 2-methyl-5-ethylpyrazine, 2-methyl-6-ethylpyrazine, etc.

The concentration of the alkyl-substituted heteroaromatic compound in the gaseous reaction mixture may be from 0.15 to 7% by mole. In the reaction mixture, the molar ratio of molecular oxygen and the ammonia is not larger than 1.6:1, preferably not larger than 1.3:1. When said molar ratio exceeds 1.6:1, undesirable reactions such as perfect combustion of the alkyl-substituted compound and ammonia occur. Thereby, the yield of the desired nitrile greatly decreases.

As molecular oxygen, air is preferably used although pure oxygen or a mixture of pure oxygen and air may be used.

The gaseous reaction mixture containing the alkyl-substituted heteroaromatic compound, molecular oxygen and ammonia may be diluted with an inactive gas such as steam or nitrogen.

In the process according to the present invention, the reaction temperature is from 300° to 650° C., preferably from 350° to 600° C. The space velocity is from 200 to 50,000 hr$^{-1}$, preferably from 300 to 20,000 hr$^{-1}$. Usually, the reaction according to the present invention is carried out under atmospheric pressure, although it may be carried out under reduced or high pressure. The reaction of the present invention is generally performed with a fixed bed reactor, although it may be performed with a fluidized bed reactor.

The present invention will be hereinafter explained further in detail by following examples, in which a conversion and a yield are calculated by following equations:

Convertion (%) = 100 ×

$$\frac{\text{Reacted alkyl-substituted heteroaromatic compound (mole)}}{\text{Supplied alkyl-substituted heteroaromatic compound (mole)}}$$

Yield (%) = 100 ×

$$\frac{\text{Produced nitrile compound (mole)}}{\text{Supplied alkyl-substituted heteroaromatic compound (mole)}}$$

EXAMPLE 1

In distilled water (1,250 g) kept at 60° C., ammonium metavanadate (146.5 g) was dissolved with stirring and to the resulting solution, 85% phosphoric acid (144 g) was added and reacted for 2 hours to obtain a reaction mixture containing a precipitated yellow compound. The reaction mixture was concentrated and dried at 110° C. for 8 hours followed by calcination at 500° C. for 4 hours in the air. The resulting catalyst was beta-vanadyl phosphate (beta-VOPO$_4$), X-ray diffraction pattern of which corresponded to that in Table 1.

The catalyst (10 ml) was filled in a Pyrex glass made reactor tube having an inner diameter of 12.6 mm.

With heating the catalyst filled portion of the reactor at 420° C., a gaseous mixture of 4-methylpyridine, ammonia, air and steam (molar ratio=1:15:75:10) was flowed through the reactor at a space velocity of 3,000 hr$^{-1}$ and the reacted gaseous mixture was trapped by water for 20 minutes and analyzed by gas chromatography. Conversion of 4-methylpyridine, 99.4%. Yield of 4-cyanopyridine, 81.5%.

EXAMPLE 2

In the same manner as in Example 1 but flowing a gaseous mixture of 4-methylpyridine, ammonia, air and steam (molar ratio=1:10:10:15) through the reactor tube kept at 400° C. at a space velocity of 2,000 hr$^{-1}$, the reaction was carried out. Conversion of 4-methylpyridine, 99.5%. Yield of 4-cyanopyridine, 94.0%.

COMPARATIVE EXAMPLE 1

In the same manner as in Example 1 but flowing a gaseous mixture of 4-methylpyridine, ammonia, air and steam (molar ratio=1:2:75:10) through the reactor tube, the reaction was carried out. Conversion of 4-methylpyridine, 99.3 %. Yield of 4-cyanopyridine, 4.2%.

COMPARATIVE EXAMPLE 2

In the same manner as in Example 1 but flowing a gaseous mixture of 4-methylpyridine, ammonia, air and steam (molar ratio=1:8:75:10) through the reactor tube at a space velocity of 2,000 hr$^{-1}$, the reaction was carried out. Conversion of 4-methylpyridine, 99.4%. Yield of 4-cyanopyridine, 9.6%.

EXAMPLE 3

To 85% phosphoric acid (63 g) heated to a temperature of 95° to 100° C., vanadium pentoxide (50 g) was added to obtain a reaction mixture containing yellow precipitates of $VOPO_4.2H_2O$. The reaction mixture was concentrated and dried at 110° C. for 8 hours followed by calcination at 500° C. for 6 hours and at 700° C. for 4 hours in the air. The obtained catalyst was alpha-vanadyl phosphate (alpha-$VOPO_4$), X-ray diffraction pattern of which corresponded to that in Table 1.

The catalyst was mixed with silicon carbide in a volume ratio of 1:1. The mixture (10 ml) was then filled in a Pyrex glass made reactor tube having an inner diameter of 12.6 mm.

With heating the catalyst filled portion of the reactor at 450° C., a gaseous mixture of 2-methylpyridine, ammonia, air and steam (molar ratio=1:10:10:10) was flowed through the reactor at a space velocity of 3,000 $hr^{-1}$. After 10 hour reaction, the reacted gaseous mixture was analyzed by gas chromatography. Conversion of 2-methylpyridine, 93.8%. Yield of 2-cyanopyridine, 76.3%.

EXAMPLE 4

To distilled water (600 ml), 85% phosphoric acid (252.8 g) was added with stirring, and after heated to 95° C., vanadium pentoxide (200 g) was added and reacted for 30 minutes. After adding silica (132 g), the reaction mixture was stirred for one hour and concentrated to obtain a reaction mixture containing a precipitated compound. The precipitated compound was dried at 110° C. for 8 hours followed by calcination at 500° C. for 6 hours and at 700° C. for 4 hours in the air. The resulting catalyst was beta-vanadyl phosphate/silica. X-ray diffraction pattern of beta-vanadyl phosphate (beta-$VOPO_4$) corresponded to that in Table 1.

The catalyst was filled in the reactor tube in the same manner as in Example 1. With heating the catalyst filled portion of the reactor at 430° C., ammonia was flowed at a rate of 100 ml/min. for 20 hours to reduce the catalyst. Then, at the same temperature, a gaseous mixture of methylpyrazine, ammonia, air and steam (molar ratio=1:20:11:1) was flowed through the reactor at a space velocity of 1,000 $hr^{-1}$ and the reacted gaseous mixture was analyzed by gas chromatography. Conversion of methylpyrazine, 94.8%. Yield of cyanopyrazine, 81.5%.

After 1,000 hour reaction, the conversion of methylpyrazine, and the yield of cyanopyrazine were 91.5% and 81.2%, respectively.

EXAMPLE 5

In distilled water (750 g), oxalic acid (315 g) was dissolved with stirring and to the resulting solution heated at 80° C., vanadium pentoxide (90.5 g) and then ammonium dihydrogenphosphate (115 g) were added followed by evaporation to dryness. The resulting solid was calcined at 550° C. for 5 hours in nitrogen to obtain vanadyl pyrophosphate (($VO)_2P_2O_7$), X-ray diffraction pattern of which corresponded to that in Table 1.

In the same manner as in Example 2 but using this vanadyl pyrophosphate as a catalyst, 3-methylpyridine as a starting material and flowing the gaseous mixture at a space velocity of 1,000 $hr^{-1}$, the reaction was carried out. Conversion of 3-methylpyridine, 90.3%. Yield of 3-cyanopyridine, 81.1%.

EXAMPLE 6

In a 10% by weight aqueous solution of monoethanolamine (1,500 g), ammonium metavanadate (146.5 g) was dissolved with stirring and then 85% phosphoric acid (144.0 g) was added and reacted for 30 minutes. The resulting solution was evaporated to dryness to obtain a solid compound, which was calcined in the air at 550° C. for 5 hours in the air to obtain a vanadium-phosphorus oxide ($VPO_5$), X-ray diffraction pattern of which showed that this oxide was amorphous.

In the same manner as in Example 2 but using this vanadium-phosphorus oxide as a catalyst and heating the reactor tube at 500° C., the reaction was carried out. Conversion of 4-methylpyridine, 96.5%. Yield of 4-cyanopyridine, 85.1%.

After 500 hours from the start of the reaction, the conversion of 4-methylpyridine was 95.4%, and the yield of 4-cyanopyridine was 84.7%.

EXAMPLES 7–9

In the same manner as in Example 2 but using a catalyst having a composition as shown in Table 2 which had been prepared by the same manner as in Example 6, the reaction was carried out. The results are shown in Table 2.

TABLE 2

| Example No. | Catalyst | Conversion of 4-picoline (%) | Yield of 4-cyanopyridine (%) |
|---|---|---|---|
| 7 | $VP_{0.75}O_{4.375}$ | 99.8 | 80.2 |
| 8 | $VP_{1.2}O_{5.5}$ | 93.1 | 85.0 |
| 9 | $VP_{1.5}O_{6.25}$ | 91.3 | 83.4 |

EXAMPLES 10–13

By using beta-$VOPO_4/3SiO_2$ prepared by the same method as in Example 4, a reaction of 2-methylpyridine, 3-methylpyridine, 4-methylpyridine or methylpyrazine was carried out under the conditions specified in Table 3. The results are also shown in Table 3.

TABLE 3

| Example No. | Raw material | Molar ratio*[1] | Space velocity ($hr^{-1}$) | Reactor temp. (%) | Conversion (%) | Yield of nitrile (%) |
|---|---|---|---|---|---|---|
| 10 | 2-Methylpyridine | 1/10/15/10 | 2,500 | 430 | 97.6 | 79.3 |
| 11 | 3-Methylpyridine | 1/2/11/13 | 1,800 | 420 | 96.1 | 82.3 |
| 12 | 4-Methylpyridine | 1/2/11/13 | 2,000 | 420 | 99.9 | 92.3 |
| 13 | Methylpyrazine | 1/25/15/2 | 1,200 | 430 | 98.6 | 83.5 |

Note:
*[1]Molar ratio of the raw material/ammonia/air/steam.

EXAMPLE 14

By using the catalyst prepared in Example 4, a mixture of 65% by mole of 3-methylpyridine and 35% by mole of 4-methylpyridine as raw materials, the reaction was carried out at a reactor temperature of 430° C., at a space velocity of 1,200 $hr^{-1}$ with a molar ratio of the raw materials, ammonia, air and steam shown in Table 4. The results are also shown in Table 4.

TABLE 4

| Molar ratio of raw materials/ ammonia/air/ steam | Conversion (%) | | Yield (%) | |
|---|---|---|---|---|
| | 3-Methyl-pyridine | 4-Methyl-pyridine | 3-Cyano-pyridine | 4-Cyano-pyridine |
| 1/5/10/15 | 98.7 | 100 | 79.9 | 90.1 |
| 1/5/4/15 | 51.5 | 100 | 37.3 | 90.3 |

EXAMPLE 15

In water (0.5 l), ammonium metavanadate (24 g) and antimony trioxide (60 g) were suspended. To the resulting suspension, 85% phosphoric acid (23.8 g) was added and heated and then silica (74 g) as a carrier was added and further heated to concentrate the suspension to obtain a paste, which was evaporated to dryness. The residue was calcined at 750° C. for 3 hours in the air. The obtained catalyst had a composition of $VSb_2P_{0.85}O_{7.62}$.

The catalyst (25 ml) was filled in the reactor tube in the same manner as in Example 1. The reactor tube was then heated at 420° C.

A gaseous mixture of methylpyrazine, ammonia, air and steam in a molar ratio of 1:19:9:5 was flowed through the reactor at a space velocity of 850 $hr^{-1}$. Conversion of methylpyrazine, 99%. Yield of cyanopyrazine, 86%.

EXAMPLE 16

In the same manner as in Example 15 but flowing a gaseous mixture of 2-methylpyridine, ammonia, air and steam in a molar ratio of 1:10:15:15 at a space velocity of 3,000 $hr^{-1}$, the reaction was carried out. Conversion of 2-methylpyridine, 99%. Yield of 2-cyanopyridine, 73%.

EXAMPLE 17

In the same manner as in Example 15 but flowing a gaseous mixture of 4-methylpyridine, ammonia, air and steam in a molar ratio of 1:5:10:9 at a reactor temperature of 340° C., at a space velocity of 3,000 $hr^{-1}$, the reaction was carried out. Conversion of 4-methylpyridine, 99%. Yield of 4-cyanopyridine, 96%.

After 500 hours, the yield was 92.3%.

EXAMPLE 18

In the same manner as in Example 4 but flowing a gaseous mixture of 3,5-dimethylpyridine, ammonia and air in a molar ratio of 1:40:40 at a reactor temperature of 420° C., at a space velocity of 1,500 $hr^{-1}$, the reaction was carried out. Conversion of 3,5-dimethylpyridine, 100%. Yield of 5-cyano-3-methylpyridine, 32.5%. Yield of 3,5-dicyanopyridine, 44.0%.

What is claimed is:

1. A process for preparing a heteroaromatic nitrile comprising catalytically reacting at least one alkyl-substituted heteroaromatic compound selected from the group consisting of alkyl-substituted pyridines and alkyl-substituted pyrazines with molecular oxygen and ammonia in a molar ratio of oxygen to ammonia not larger than 1.6:1 in a gaseous phase in the presence of an oxide catalyst or a hydrated oxide catalyst wherein the active catalytic component consists essentially of the formula:

$$VP_xSb_yO_z \qquad (I)$$

wherein x, y and z represent atomic ratios of phosphorus, antimony and oxygen to vanadium, respectively, and x is from 0.1 to 5, y is 0 to 8 and z is defined from the valencies of vanadium, phosphorus and antimony and the values of x and y.

2. The process according to claim 1, wherein the oxide is a crystalline vanadium-phosphorus oxide of the formula (I) wherein y is 0 (zero) and the atomic ratio of vanadium and phosphorus is 1, or a reduction product of said vanadium-phosphorus oxide.

3. The process according to claim 2, wherein the crystalline oxide is an oxide of the formula:

$$(VO)_nP_nO_{4n-1} \cdot xH_2O \qquad (II)$$

wherein n is an integer not less than 2 and x is 0 or a positive integer.

4. The process according to claim 2, wherein the crystalline vanadium-phosphorus oxide is at least one oxide selected from the group consisting of alpha-vanadyl phosphate (alpha-$VOPO_4$), alpha-vanadyl phosphate dihydrate (alpha-$VOPO_4 \cdot 2H_2O$), beta-vanadyl phosphate (beta-$VOPO_4$), vanadyl pyrophosphate (($VO)_2P_2O_7$) and vanadyl pyrophosphate hydrate (($VO)_2H_4P_2O_9$ or ($VO)_2P_2O_7 \cdot 2H_2O$).

5. The process according to claim 1, wherein the catalyst is carried on a carrier selected from the group consisting of silica, alumina, silicon carbide, titanium oxide, diatomaceous earth and zeolite.

6. The process according to claim 2, wherein the catalyst is carried on a carrier selected from the group consisting of silica, alumina, silicon carbide, titanium oxide, diatomaceous earth and zeolite.

7. The process according to claim 2, wherein the reduction product of said vanadium-phosphorus oxide is a reduction product prepared by reducing said vanadium-phosphorus oxide with ammonia or an ammonia-containing gas at a temperature of 300° to 600° C.

* * * * *